United States Patent [19]

Coss et al.

[11] Patent Number: 5,683,246
[45] Date of Patent: Nov. 4, 1997

[54] ILLUMINATION APPARATUS FOR DENTAL HANDPIECE

[75] Inventors: Ronald G. Coss, Newport Beach; Jay R. McCoy, Trabuco Canyon, both of Calif.

[73] Assignee: Micro Motors, Inc., Santa Ana, Calif.

[21] Appl. No.: 424,871

[22] Filed: Apr. 17, 1995

[51] Int. Cl.$^6$ .................... A61C 1/00; A61C 3/00
[52] U.S. Cl. ................................................. 433/29
[58] Field of Search ............................................ 433/29

[56] References Cited

U.S. PATENT DOCUMENTS

| | | | |
|---|---|---|---|
| 2,539,828 | 1/1951 | Goldis et al. | 433/29 X |
| 3,634,938 | 1/1972 | Hutchinson | 433/29 |
| 4,334,863 | 6/1982 | Magid et al. | 433/29 |
| 4,398,885 | 8/1983 | Loge et al. | 433/26 |
| 4,514,169 | 4/1985 | Strohmaier | 433/29 |
| 4,515,564 | 5/1985 | Lohn | 433/126 |
| 4,518,355 | 5/1985 | Hoffmeister et al. | 433/29 |
| 4,519,780 | 5/1985 | Strohmaier et al. | 433/29 |
| 4,578,033 | 3/1986 | Mossle et al. | 433/29 |
| 4,614,414 | 9/1986 | Gores | 433/29 X |
| 4,642,051 | 2/1987 | Lohn | 433/100 |
| 4,648,838 | 3/1987 | Schlachter | 433/29 |
| 4,886,455 | 12/1989 | Lohn | 433/80 |
| 4,902,225 | 2/1990 | Lohn | 433/80 |
| 5,096,418 | 3/1992 | Coss | 433/29 |
| 5,267,857 | 12/1993 | Sickler | 433/29 |
| 5,332,389 | 7/1994 | Rosenstatter | 433/29 |

*Primary Examiner*—Nicholas Lucchesi
*Attorney, Agent, or Firm*—Knobbe, Martens, Olson & Bear, LLP.

[57] ABSTRACT

The present invention relates to a surgical drilling system having a light source for illuminating the treatment area during surgery. The light source is detachably connected to a light guide assembly which is mounted on the handpiece of a surgical drilling system. Light from a lens-end subminiature incandescent bulb is focused on an optical fiber bundle in the light guide assembly. The incandescent bulb generates less heat and has a greater rated life than a halogen bulb with comparable light intensity at the operation site.

In one embodiment the light source controller utilizes a switching power regulator with pulse width modulation. The light source controller converts a pulse width modulation signal into a DC voltage. The duty cycle of the signal increases from a minimum to a maximum, thereby providing a soft start for the lamp. In normal operation, the duty cycle creates an average lamp drive voltage which is less than the maximum lamp drive voltage. The soft start and average lamp power extend the useful life of the bulb by reducing the stress on the filament caused by sudden increases in the drive voltage.

2 Claims, 5 Drawing Sheets

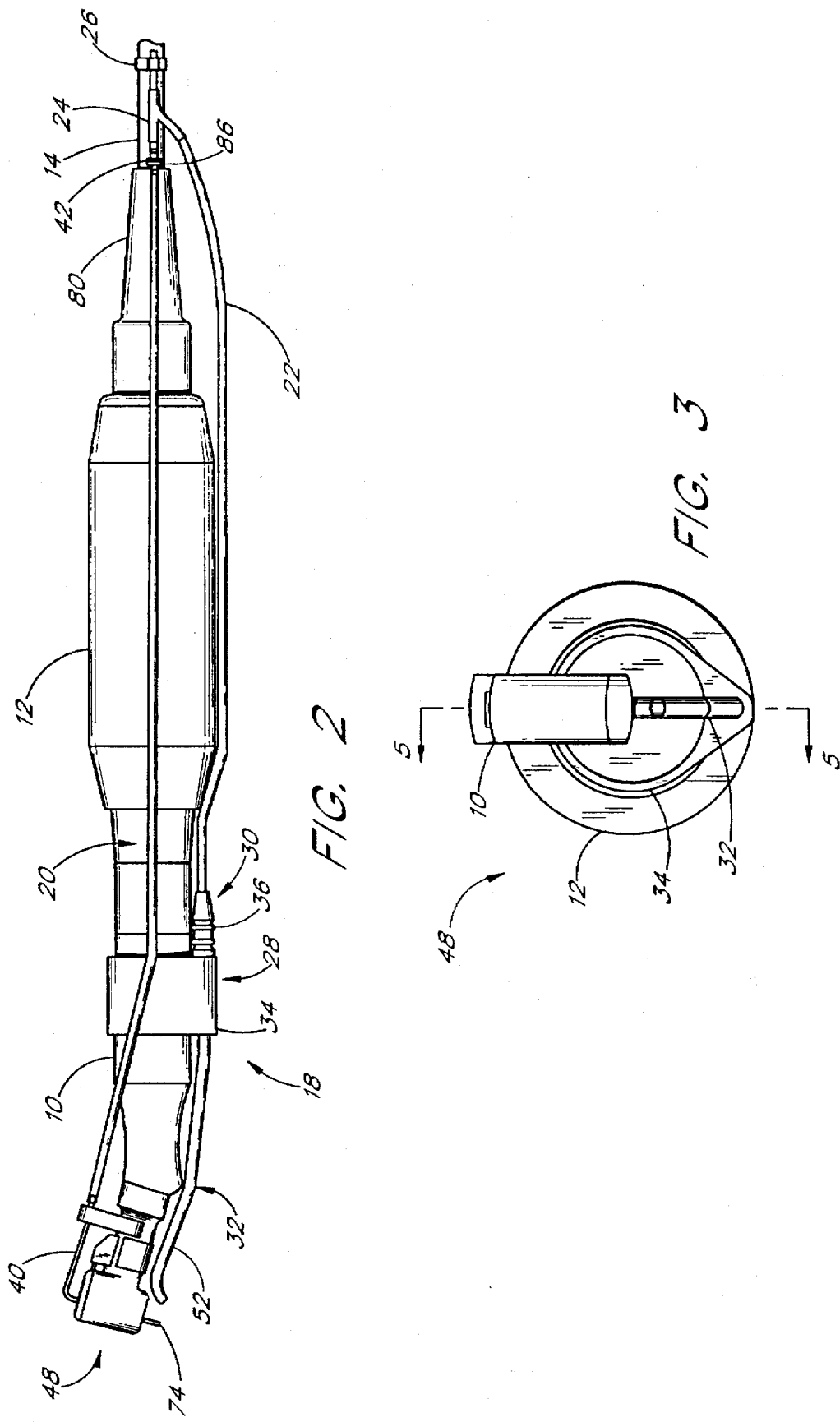

| FUEL LOGIC STATE | CONTROL SIGNAL |
| --- | --- |
| TOUCH POINT | ZERO |
| DIRECT | EQUAL TO THL |
| LAUNCH | RAMP TO HOLD AT % THL |
| RAMP | RAMP TO THL |
| EXTENDED DIRECT | EQUAL TO THL/$THL_{REF}$ |

FIG. 5B

ILLUMINATION APPARATUS FOR DENTAL HANDPIECE

FIELD OF INVENTION

The present invention relates to an apparatus for providing illumination in a surgical drilling system, particularly in the field of oral surgery, and even more particularly in the field of implantology.

BACKGROUND OF INVENTION

Surgical drilling systems commonly comprise a motor controller, a motor and a handpiece, with a gear train and a tool bit.

A common method of illuminating the surgical treatment site is with a halogen lamp. Light from the lamp is transmitted through a bendable light guide that is detachably connected to a rigid light guide within the handpiece. The light is emitted from an opening in the handpiece near the tool bit.

To compensate for the attenuation of the light intensity through these light guides, a high intensity lamp such as a 100 Watt halogen bulb is typically used. Halogen bulbs produce higher light intensity than ordinary filament bulbs and are commonly used in such applications.

A typical bulb life for a halogen lamp is relatively short (e.g. 1000 hours) as compared to a typical bulb life (e.g. 40,000 hours) for an incandescent lamp. Additionally, a halogen lamp must reach a temperature of 250 degrees C. before the halogen cycle begins to operate. The lamp thus generates substantial amounts of heat. In some cases a fan is needed to cool the lamp housing.

The heat generated by a halogen bulb presents a safety hazard unless it is located a sufficient distance away from the operation site. If the halogen bulb is located near the operating site, there is a risk that the patient or the surgeon will be burned by the lamp.

SUMMARY OF INVENTION

The present invention comprises an illumination system for a surgical drilling apparatus, such as a dental apparatus comprising a handpiece detachably mounted to a motor. A light guide assembly, mounted to the handpiece, comprises a light guide and a cavity configured to receive a light source. The cavity is disposed to input light from the light source into the light guide. Preferably the source is an incandescent source.

Another aspect of the present invention is a method of mounting an illumination system for a surgical drilling apparatus comprising a motor and a detachably mounted handpiece. The steps comprise mounting a light guide assembly on a handpiece, mounting a light source in a cavity of the light guide assembly such that the light source is readily detachable from the cavity, and positioning the light guide assembly so that the light guide conducts light from the cavity to a location proximal to an end of the handpiece.

A major advantage of the present invention is that the light guide is relatively short (e.g. no longer than the length of the handpiece) and thus, there is very little attenuation of the light as it passes through the light guide. The low attenuation characteristics permit the use of an incandescent light source rather than the prior art halogen bulb light source. For a given level of light intensity at the operation site, the incandescent source produces less heat. It does not require a cooling mechanism, and there is little if any likelihood of the operator being accidentally burned. Additionally, the life of an incandescent light source is longer than the life of a halogen bulb of similar wattage.

Another advantage of the present invention is the ease with which the light source can be disconnected from the light guide on the handpiece. As handpieces are changed during a surgical procedure, the light source is readily detachable from the light guide assembly of the handpiece and readily attachable to the light guide assembly of another handpiece.

In a one embodiment, the dental apparatus additionally comprises a motor controller for driving the motor and a separate lamp controller which supplies a Direct Current (DC) voltage to power the lamp. The lamp controller uses a pulse width modulation (PWM) controlled DC converter circuit to supply power for the lamp. By using a PWM controlled circuit, the pulse width can be increased slowly at turn on which causes the DC voltage to the lamp to slowly increase. The effect of slowly increasing the voltage at turn on is a reduced shock-induced stress to the filament of the bulb.

BRIEF DESCRIPTION OF THE DRAWINGS

FIG. 2 is an enlarged elevational view of the dental handpiece of FIG. 1, showing the illumination apparatus mounted thereon.

FIG. 3 is an elevational view of the dental handpiece of FIG. 2, showing the distal end of the handpiece.

FIG. 6 is a functional block diagram of a light source controller.

DETAILED DESCRIPTION OF THE PREFERRED EMBODIMENTS

Figure 1:
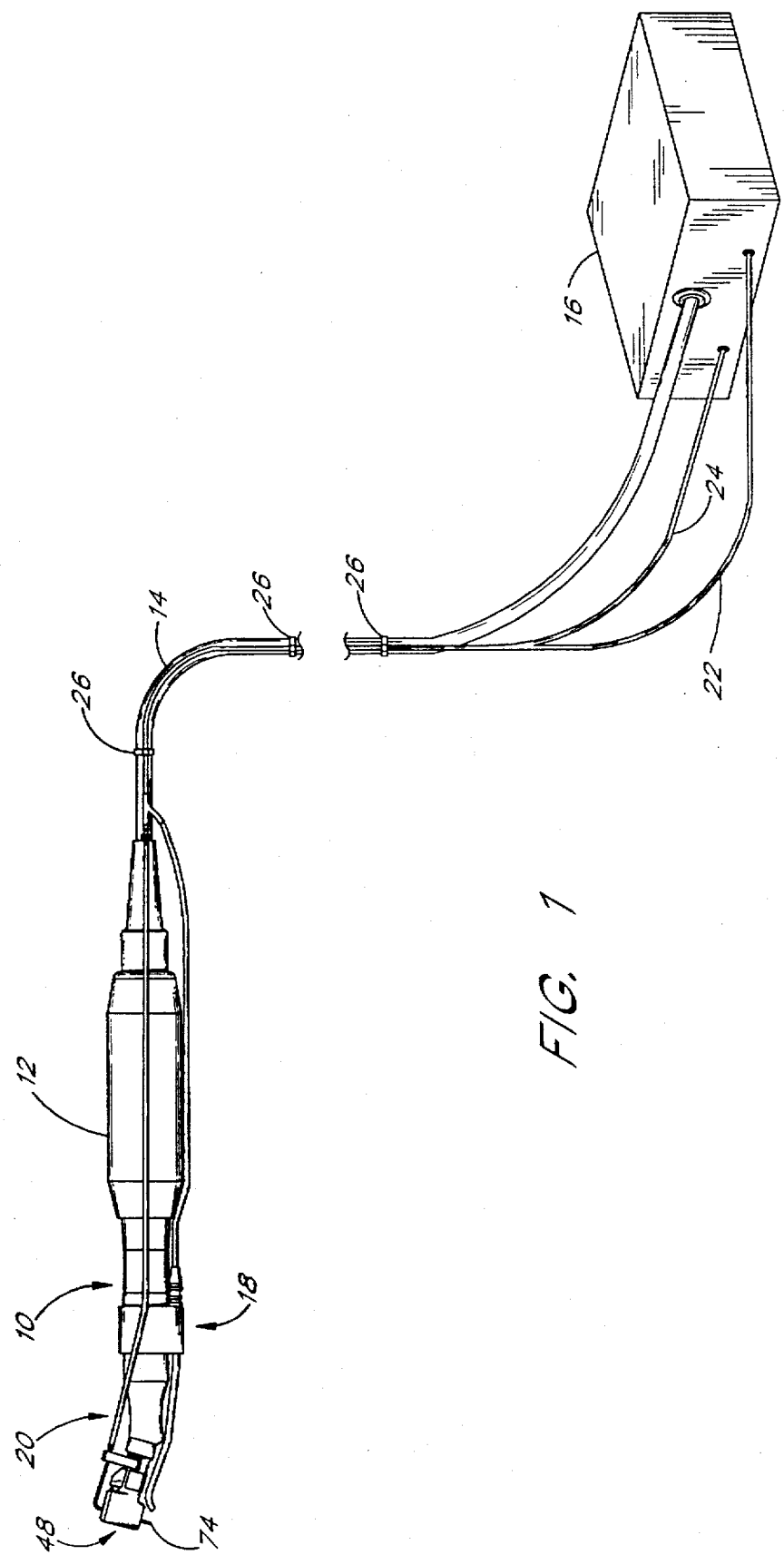
FIG. 1 is a perspective view of a dental drilling system comprising a motor electrically connected to a motor controller and a handpiece mechanically attached to the motor.

As shown in FIG. 1, the preferred embodiment comprises a handpiece 10, a motor 12, a motor cable 14, a motor controller 16, an illumination system 18 and an irrigation system 20. The motor 12 is connected to the motor controller 16 by the motor cable 14 and the handpiece 10 is detachably connected to the motor 12. The motor controller 16 supplies control signals and power to the motor 12, via the motor cable 14, and the motor 12 drives the gear train of the handpiece 10 for driving a tool such as a bit 74. The motor controller 16 is described in detail in co-pending U.S. application Ser. No. 08/158,236, filed Nov. 26, 1993, which is hereby incorporated by reference herein.

As shown in FIGS. 1 to 3, an irrigation system 20 is mounted on the handpiece 10 to provide fluid for irrigating the operation site at the bit 74. The irrigation system comprises an irrigation tube 24 connected to the motor controller 16, an irrigation nozzle assembly 40, a male connector 42 and a mating female connector 86. A controlled fluid flow is supplied to the irrigation system 20 by the motor controller 16. In a preferred embodiment, the male connector 42 comprises a male luer fitting and the female connector 86 comprises a female luer fitting. The irrigation tube 24 is connected to one end of the male connector 42 while the other end of the male connector 42 is mated with an end of the female connector 86. One end of the irrigation nozzle assembly 40 is connected to the other end of the female connector 86, and the other end of the irrigation nozzles assembly 40 is attached to the handpiece 10 above the bit 74 and positioned to irrigate the operation site.

Referring to FIGS. 2 to 5, the illumination system 18 is mounted on the handpiece 10 to illuminate a site proximate to the bit 74. The system 18 comprises a light source power cord 22 electrically connected to the motor controller 16. The light source power cord 22 and the irrigation tube 24 are strapped to the motor cable 14 by a plurality of clips 26. A controlled amount of electrical power is supplied to the illumination system 18 by the motor controller 16.

The illumination system 18 additionally comprises a light source 30 connected to the light source power cord 22 and a light guide assembly 28. The light source 30 comprises a bulb 50 which has a power lead 62 and a return lead 64, a tubular lamp bushing 36, a compressible ring 66 which is mounted in a groove 76 on the lamp bushing 36, and a grip area 78 which is located on the surface of the lamp bushing 36. The bulb 50 further comprises a lens 82 which is molded directly onto the distal end of the bulb 50 during the manufacturing process of the bulb 50. The lens 82 which has a focal length f, increases light output 10 times as compared to an equivalent bulb without a lens. The bulb 50 is mounted in the center bore of the lamp bushing 36 and is retained therein by epoxy adhesive applied to the base of the bulb 50. The lens 82 and a distal end 84 of the lamp bushing 36 are separated by the focal length, f.

The light source power cord 22 comprises a stiff plastic tube 56, a jacket 54, a light source power line 58 and a light source return line 60. The light source power line 58 and the light source return line 60 electrically connect the motor controller 16 to the power lead 62 and the return lead 64 of the bulb 50, respectively, and are internal to the jacket 54. Epoxy adhesive is applied to cover the connection of the light source power line 58 with the power lead 62 and the connection of the light source return line 60 with the return lead 64. The stiff plastic tube encases the jacket from the proximal end portion 80 of the motor 12 to the lamp bushing 36.

The light guide assembly 28 comprises a light guide 32, a fiber optic clip or holder 34, and a tubular light guide bushing 46. The light guide 32 comprises a rigid tube 52 and a fiber optic bundle 68 comprised of plural optical fibers that extend in the rigid tube 52 along its entire length. One end of the rigid tube 52 is mounted in a center bore of the light guide bushing 46 and extends along the entire length of the bushing 46. The outer diameter of the rigid tube 52 is substantially equal to the inner diameter of the light guide bushing 46, and the rigid tube 52 is retained in the bore by interference fit. The light guide bushing 46 is mounted in one end of a bore extending longitudinally through the fiber optic clip 34 (i.e. in a direction parallel to the longitudinal axis of the handpiece.) The outer diameter of the light guide bushing 46 is substantially equal to the diameter of the bore in the fiber optic clip 34 and the bushing 46 is retained in the bore by interference fit. The light guide bushing 46 is positioned at one end of the bore of the fiber optic clip 34 so that a cavity 44 is formed at the other end. The cavity 44 has a mouth that opens toward the rear of the handpiece 10 and includes a circumferential groove 70 between the mouth and the bushing 46. The fiber optic clip 34 has a pair of curved arm portions that extend from a central portion circumferentially around the handpiece 10. The arm portions are sized to retain the fiber optic clip 34 on the handpiece by the spring action of the arms. The light guide 32 is positioned to extend from the fiber optic clip 34 to the distal end 48 of the handpiece 10, terminating proximate to the bit 74.

Figure 5:
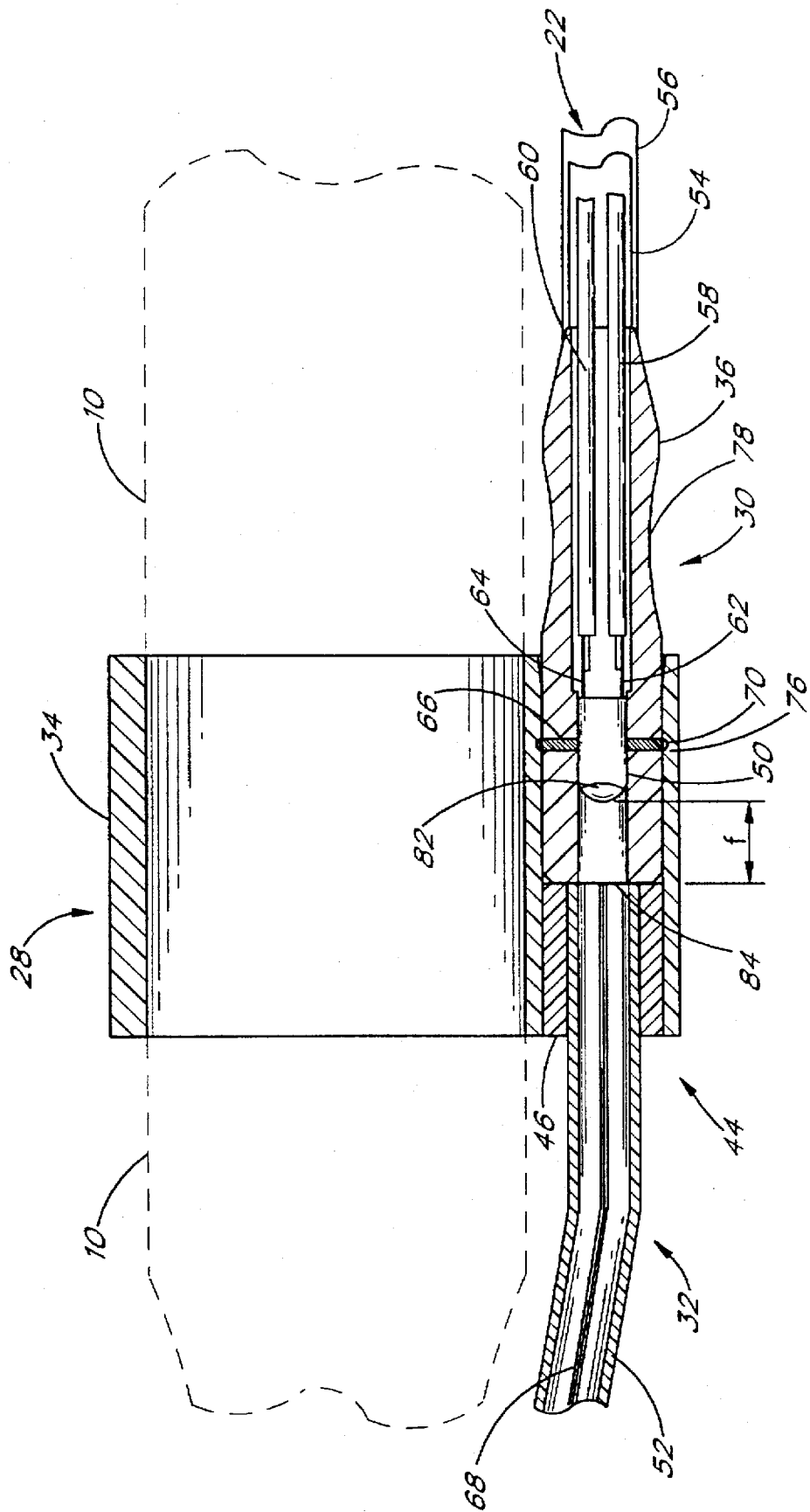
FIG. 5 is a partial cross sectional view taken along the lines 5—5 of FIG. 3 showing the light source mounted in the cavity of the light guide assembly.

Referring to FIG. 5, the light source 30 is sized and configured to permit it to be slidably mounted in the cavity 44. Upon insertion of the light source 30 into the cavity 44, the compressible ring 66 on the lamp bushing 36 is compressed. When it aligns with the groove 70, the compressible ring 66 expands into the groove 70 by spring force. The compressible ring 66 has sufficient spring force to permit the light source 30 to be firmly retained in the cavity 44 while being readily compressible to permit the light source 30 to be removed from the cavity 44 by applying a manual pulling force on the lamp bushing (e.g. by gripping it between a thumb and forefinger). The lamp bushing 36 is sized so that when the ring 66 is in the groove 70, the light guide bushing 46 and the lamp bushing 36 abut. The lens 82 is fixedly mounted in the lamp bushing 36 so that the distance between the lens 82 and the junction of the light guide bushing 46 and the lamp bushing 36 is equal to the focal length f of the lens 82. Since an end of the fiber bundle 68 is located at such junction, the light from the bulb 50 will focus on the end of the light guide 32, thereby efficiently coupling the white light from the bulb 50 to the fiber optic bundle 68 of the light guide 32.

In a preferred embodiment the bulb 50 is a T-¾ subminiature incandescent lens-end lamp with a coil centered filament, GILWAY part number 4115-1 which is commercially available from GILWAY TECHNICAL LAMP, 800 West Commings Park, Woburn, Mass. 01801. The mean spherical candle power of the bulb is 0.150 candela at the design voltage of 5 volts and the life of the bulb at the design voltage of 5 volts is 40,000 hours. An optical lens is molded directly onto the bulb.

The parts listed in the following table are used in a preferred embodiment of the surgical drilling system.

| MICRO MOTORS PART NUMBER | DESCRIPTION |
| --- | --- |
| 28901 | IRRIGATION NOZZLE ASSEMBLY |
| 3122 | FEMALE LUER FITTING |
| 3121-2 | MALE LUER FITTING |
| 3468 | CLIP |
| 5426 | IRRIGATION TUBE |
| 4521 | LIGHT GUIDE BUSHING |
| A4520 | LIGHT GUIDE |
| 4523 | LAMP BUSHING |
| 4522 | FIBER OPTIC CLIP |
| 5430 | COMPRESSIBLE RING |
| 5432 | LIGHT SOURCE POWER LINE AND LIGHT SOURCE RETURN LINE, TEFLON JACKET 28 GAUGE WIRE |
| 5424 | STIFF PLASTIC TUBE, 15 GAUGE TEFLON TUBING |
| 29502 | MOTOR CABLE |
| 29503 | MOTOR |
| 28181 | HANDPIECE |

All of the above parts are commercially available from MICRO MOTORS, 151 East Columbine Avenue, Santa Ana, Calif. 92707.

A preferred use for the surgical drilling system disclosed herein is implantology. The field of implantology involves replacement of natural teeth with artificial teeth that are secured to the jaw bone of the patient. The implant procedure involves different tools, such as drill bits and tapping bits, to perform the steps necessary to attach the artificial teeth. Typically, each tool is attached to the handpiece with an appropriate gear train for that tool and the oral surgeon typically changes handpieces a number of times during surgery.

Figure 4:
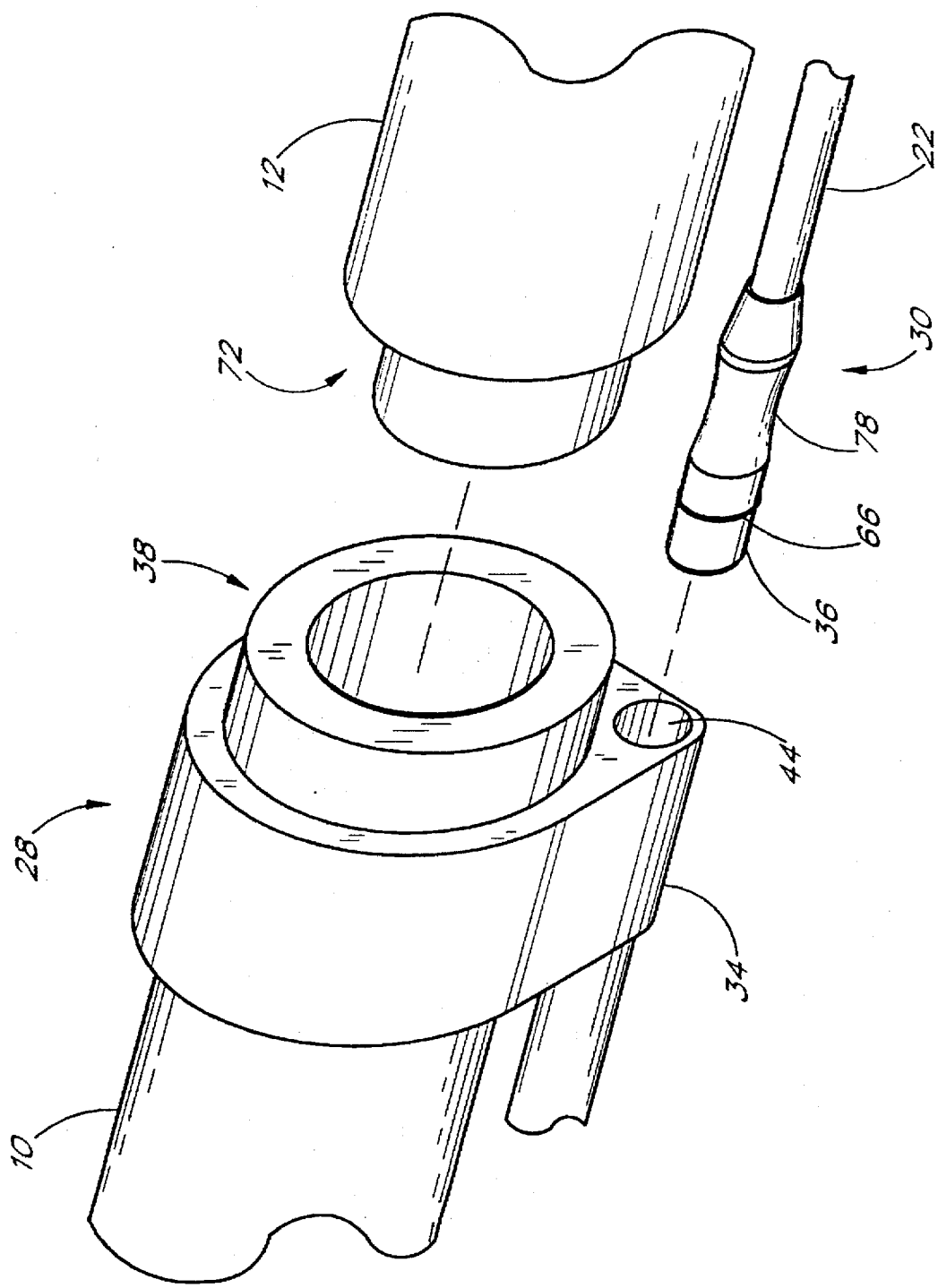
FIG. 4 is a fragmentary perspective view of the proximal end portion of the handpiece and the distal end portion of the motor, illustrating the detachable connection between the light source and the cavity of the light guide assembly.

Referring to FIGS. 2 and 4, to change handpieces the handpiece 10 is mechanically disconnected from the motor 12 by gripping the handpiece 10 and manually pulling the handpiece 10 from the motor 12 until a spring clip (not shown) at the base of the distal end 72 of the motor 12 disengages from a mating recessed groove (not shown) in the proximal end 38 of the handpiece 10. When the motor 12 and the handpiece 10 are separated, the irrigation system 20 and the illumination system 18, both of which bridge across the motor/handpiece junction, are separated into two portions.

The two portions of the irrigation system 20 may be separated at the interface of the male connector 42 and the female connector 86. The portion of the irrigation system 20 comprising the irrigation nozzle assembly 40 and the female connector 86 remain with the handpiece 10, while the portion of the irrigation system 20 comprising the irrigation tube 24 and the male connector 42 remain with the motor 12 and motor cable 14. To detach the irrigation nozzle assembly from the irrigation tube 24, the male connector 42 is manually rotated relative to the female connector 86 until the connectors separate. The irrigation tube 24 is attached by clips 26 to the motor cable 14.

The two parts of the illumination system 18 may be separated at the interface of the light source 30 and the light guide assembly 28. The light guide assembly 28 remains with the handpiece 10 while the light source 30 remains with the motor 12 and motor cable 14. To detach the light source 30 from the light guide assembly 28, force is applied to the lamp bushing 36 by grasping (i.e. between the thumb and forefinger) the lamp bushing 36 in the grip area 78 and gently pulling such that the compressible ring 66 on the lamp bushing 36 is compressed and disengages from the groove 70 in the cavity 44. Further pulling will then cause the light source 30 to slide out of the bore of the fiber optic clip 34 and thus out of the cavity 44. The light source power cord 22 is attached by clips 26 to the motor cable 14. The light source 30, which is at an end of the light source power cord 22, is loosely supported by the stiff plastic tube 56.

The handpiece 10 with the attached light guide assembly 28, the irrigation nozzle assembly 40 and the female connector 86 is exchanged for a second handpiece 10 with its attached light guide assembly 28, its irrigation nozzle assembly 40 and its female connector 86. The second handpiece 10 has the appropriate tool bit and gearing for the next step of the oral surgery procedure. The second handpiece 10 is attached to the motor 12 by manually pushing the motor 12 into the handpiece 10. A shaft at the distal end 72 of the motor 12 slides into a receptacle at the proximal end of the handpiece 10 until the spring clip (not shown) on the shaft mates with the matching recessed groove (not shown) in the receptacle. The shaft at the distal end 72 of the motor 12 and the receptacle at the proximal end 38 of the handpiece 10 form a spring loaded self-aligning connection.

To reconnect the irrigation system 20, an end of the female connector 86 on the irrigation nozzle assembly 40 and an end of the male connector 42 on the irrigation tube 24 are manually connected together. To reconnect the illumination system 18, the light source 30 is inserted into the cavity 44 of the second handpiece 10 by grasping the grip area 78 of the lamp bushing 36 and pushing the lamp bushing 36 into the cavity 44 until the compressible ring 66 is engaged in the groove 70.

The foregoing procedure is repeated whenever the surgeon changes handpieces during the surgery.

In one preferred embodiment, the motor controller 16 utilizes a switching power regulator with pulse width modulation (PWM), and includes a light source controller 90 as illustrated in FIG. 6. The light source controller 90 comprises a lamp driver circuit 92, a current sensor circuit 94, a light source pulse width modulation line 96, a light source power line 58, a light source return line 60, and a light source current line 98. The bulb 50 is connected to the light source controller 90 by the light source power line 58 and the light source return line 60. Within the light source controller 90, the lamp driver circuit 92 is connected to the motor controller 16 through the light source pulse width modulation line 96. The lamp driver circuit 92 is connected to the bulb 50 through the light source power line 58. The bulb 50 is also connected to the current sensor circuit 94 through the light source return line 60. The current sensor circuit 94 is connected to the lamp driver circuit 92 through the light source current line 98. A zero to five volt PWM signal on the light source PWM line 96 is generated by the motor controller 16 at a predetermined frequency. The PWM signal is a logic signal where zero volts represents a logic 0 and five volts represents a logic 1. The duty cycle of the PWM signal is applied to modulate the maximum voltage available to drive the bulb, thereby controlling the average voltage that is used to drive the bulb. In a preferred embodiment, the PWM frequency is 30 KHz, the maximum voltage available to drive the bulb is 24 volts DC and the duty cycle of the PWM signal is 25% during normal operation. This means that the PWM signal is five volts or a logic 1 for 25% of its 30 KHz cycle and zero volts or a logic 0 for 75% of its 30 KHz cycle. The corresponding drive voltage is 24 volts for 25% of a 30 KHz cycle and zero volts for 75% of a 30 KHz cycle or, in other words, the average drive voltage is 6 volts. When initially illuminating the bulb 50, the duty cycle of the PWM signal on the light source PWM line 96 is gradually increased from zero to approximately 25% to gradually increase the average drive voltage, and provide a soft start for the bulb 50. This gradual increase in the average drive voltage for the bulb 50 extends the useful life of conventional light sources, such as incandescent bulbs, by reducing the stress on the filament caused by sudden increases in the average drive voltage.

Normally the lamp driver circuitry 92 applies the PWM signal on the light source PWM line 96 to the light source power line 58 after transforming the signal to the correct voltage and current capacity to drive the bulb 50. The current flowing through the bulb 50 is determined by the current sensor circuit 94. A signal on the light source current line 98 is generated by the current sensor circuit 94, indicating whether the current drawn by the lamp 50 is exceeding a predetermined maximum value. The signal is received by the lamp drive circuit 92 on the light source current line 98 and the PWM signal on the light source power line 58 is disabled if an error condition exits, such as where the lamp draws excess current.

The present invention may be embodied in other specific forms without departing from its spirit, or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

We claim:

1. A surgical drilling apparatus, comprising:

a motor;

a light bulb having a filament;

a dental handpiece detachably connected to said motor, said handpiece including a light guide assembly comprising a light guide, said light guide assembly having a cavity configured to receive said light bulb, said cavity being disposed to input light from said light bulb into said light guide; and a motor controller for driving said motor, said controller comprising means for supplying a dc voltage for lighting said light bulb, said supplying means producing a pulse with modulation signal duty cycle which increases over time from a minimum to a maximum, and means for converting said pulse width modulation signal to said DC voltage for lighting said light bulb, whereby the amount of voltage supplied to said light bulb is gradually increased to reduce voltage-induced stress on the filament of the light bulb.

2. A drilling apparatus comprising:

an electric motor;

a dental handpiece having a forward end for carrying a drilling tool and having a rear end connected to a forward end of the motor by a detachable connection;

a fiber optic holder mounted on the exterior of the handpiece adjacent to the detachable connection, said holder including a cavity spaced radially outwardly from the handpiece;

a fiber optic bushing fixed in a forward end of said cavity;

a fiber optic having a rear end positioned in said bushing;

a lamp bushing having a forward end inserted within a rear end of said cavity;

a light bulb positioned in the lamp bushing spaced rearwardly from a forward face of the lamp bushing, said forward face engaging a rearward portion of said fiber optic bushing to limit the forward insertion of said lamp bushing and to space said lamp a desired distance from said fiber optic for efficiently transmitting light from said lamp into said fiber optic, said lamp bushing and lamp being removable from said cavity when said motor and said handpiece are separated by way of said detachable connection.

* * * * *